(12) United States Patent
Gayle et al.

(10) Patent No.: US 9,116,097 B2
(45) Date of Patent: Aug. 25, 2015

(54) PART FIXTURE FOR NONDESTRUCTIVE INSPECTION

(75) Inventors: David Michael Gayle, Wichita, KS (US); Adam Joseph Donar, Wichita, KS (US)

(73) Assignee: Spirit AeroSystems, Inc., Wichita, KS (US)

(*) Notice: Subject to any disclaimer, the term of this patent is extended or adjusted under 35 U.S.C. 154(b) by 380 days.

(21) Appl. No.: 13/557,392

(22) Filed: Jul. 25, 2012

(65) Prior Publication Data

US 2014/0026668 A1    Jan. 30, 2014

(51) Int. Cl.
*G01N 29/24* (2006.01)
*G01N 29/04* (2006.01)
*G01N 29/22* (2006.01)
*G01N 29/28* (2006.01)

(52) U.S. Cl.
CPC ............ *G01N 29/043* (2013.01); *G01N 29/223* (2013.01); *G01N 29/28* (2013.01); *G01N 2291/0231* (2013.01); *G01N 2291/2694* (2013.01)

(58) Field of Classification Search
USPC ............................... 73/622, 644, 632; 269/21
See application file for complete search history.

(56) References Cited

U.S. PATENT DOCUMENTS

| | | | |
|---|---|---|---|
| 4,551,192 A * | 11/1985 | Di Milia et al. .......... 156/345.51 |
| 7,379,480 B2 | 5/2008 | Balasubramanian et al. |
| 7,448,271 B2 | 11/2008 | Duncan et al. |
| 7,735,369 B2 * | 6/2010 | Young et al. .................... 73/622 |
| 2006/0151001 A1 * | 7/2006 | Satoyoshi et al. ................ 134/1 |
| 2009/0107244 A1 | 4/2009 | Fetzer et al. |
| 2009/0293647 A1 * | 12/2009 | Muneishi et al. .......... 73/864.11 |

* cited by examiner

*Primary Examiner* — Hezron E Williams
*Assistant Examiner* — Xin Zhong
(74) *Attorney, Agent, or Firm* — Hovey Williams LLP (57) ABSTRACT

An ultrasound inspection system includes a part fixture at least partially submerged in a liquid bath. The part fixture includes at least one surface with a plurality of elongated protrusions extending from the surface and a fluid flow ingress aperture in the surface. A part to be inspected is secured on the fixture by circulating the liquid through a channel in the fixture such that the liquid flows around the part and into the ingress aperture. The part engages and is supported by the elongated protrusions, wherein the elongated protrusions are configured such that they do not interfere with the ultrasonic testing performed on the part.

3 Claims, 7 Drawing Sheets

PART FIXTURE FOR NONDESTRUCTIVE INSPECTION

BACKGROUND

1. Field

Embodiments of the present invention relate to systems and methods of nondestructive inspection. More particularly, embodiments of the present invention relate to ultrasonic inspection systems and part fixtures adapted for use therewith.

2. Related Art

It is often desirable or required by law to perform a complete inspection of manufactured parts prior to shipment or use. Aircraft composite parts, for example, often require 100% inspection after manufacture to discover any defects such as excessive porosity, delamination, defective bonding, voids, and embedded foreign objects.

Nondestructive inspection is a commonly used method of performing a complete test of manufactured parts. Ultrasonic inspection is one form of nondestructive inspection that involves the use of ultrasound waves to inspect the interior portions of parts. Ultrasonic testing and other forms of nondestructive inspection are desirable in that they can be performed relatively quickly and do not require disassembly of the inspected parts.

Ultrasonic inspection equipment typically utilizes an ultrasound transducer or array of transducers (either of which may be referred to as a "probe") to generate ultrasonic waves. Ultrasonic waves are similar to sound waves but have a much higher frequency, typically well beyond the range of human hearing. During ultrasonic inspection, the ultrasound probe is positioned near the surface of the part being inspected and oriented such that ultrasound waves generated by the probe are directed toward and through the part. When an ultrasound wave encounters a discontinuity in the part, such as a void, delamination or foreign object, part of the energy in the ultrasound wave is reflected. The reflected energy travels back through the part as a second ultrasound wave and is detected by the ultrasound probe, which acts as both a transmitter and receiver in what is commonly referred to as a "pulse echo" ultrasonic test system. The reflected ultrasound waves are collected and used to create a reflection signature, which may be expressed to the user in the form of an image or graph.

Ultrasonic inspection requires that the part under inspection be firmly secured in place and remain stable during the inspection process. One method of securing a part during the inspection process involves clamping the part in place. Because the clamps used to secure the part interfere with the ultrasonic inspection, the clamps must be moved during the inspection process to allow the entire part to be completely inspected. While moving the clamps during the inspection process allows for a complete inspection of the part, this step takes time and thus renders the process inefficient. Moving the clamps also complicates automation of the inspection process.

Accordingly, there is a need for a device which overcomes the limitations described above.

SUMMARY

Embodiments of the present invention solve the above-described problems by providing a nondestructive inspection system that does not require the use of clamps or other fixtures that interfere with the inspection process.

A system for securing a part in accordance with an embodiment of the invention comprises a fixture including a surface, a plurality of protrusions extending from the surface, a fluid ingress aperture in the surface, and a pump for moving fluid through the ingress aperture. Fluid moving through the ingress aperture secures the part against at least some of the plurality of protrusions.

An ultrasound inspection system in accordance with another embodiment of the invention comprises a part fixture including a fluid flow channel, a first planar surface, a first plurality of elongated protrusions extending from the first surface, and a first fluid ingress aperture in the first surface and in fluid communication with the fluid flow channel. A second planar surface of the part fixture is at an angle of inclination relative to the first planar surface. A second plurality of elongated protrusions extend from the second surface, and a second fluid ingress aperture in the second surface is in fluid communication with the fluid flow channel. The fixture is at least partially submerged in a liquid bath and a pump moves liquid from the bath through the channel, including into the first and second fluid ingress apertures. An ultrasound probe emits ultrasonic waves toward a part secured against the fixture.

A method of nondestructive inspection of a part in accordance with yet another embodiment of the invention comprises submerging a part fixture in a liquid bath, the fixture including a surface, a plurality of protrusions extending from the surface, and a fluid ingress aperture in the surface. The part is placed on the fixture such that the part is in contact with at least some of the protrusions and is separated from the surface by a space. The part is secured against the fixture by a pressure differential created by causing liquid flow into the fluid ingress aperture, and ultrasonic inspection of the part is performed while the part is secured against the fixture.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the preferred embodiments and the accompanying drawing figures.

The drawing figures do not limit the present invention to the specific embodiments disclosed and described herein. The drawings are not necessarily to scale, emphasis instead being placed upon clearly illustrating the principles of the invention.

DETAILED DESCRIPTION

The following detailed description references the accompanying drawings that illustrate specific embodiments in which the invention may be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Figure 1:
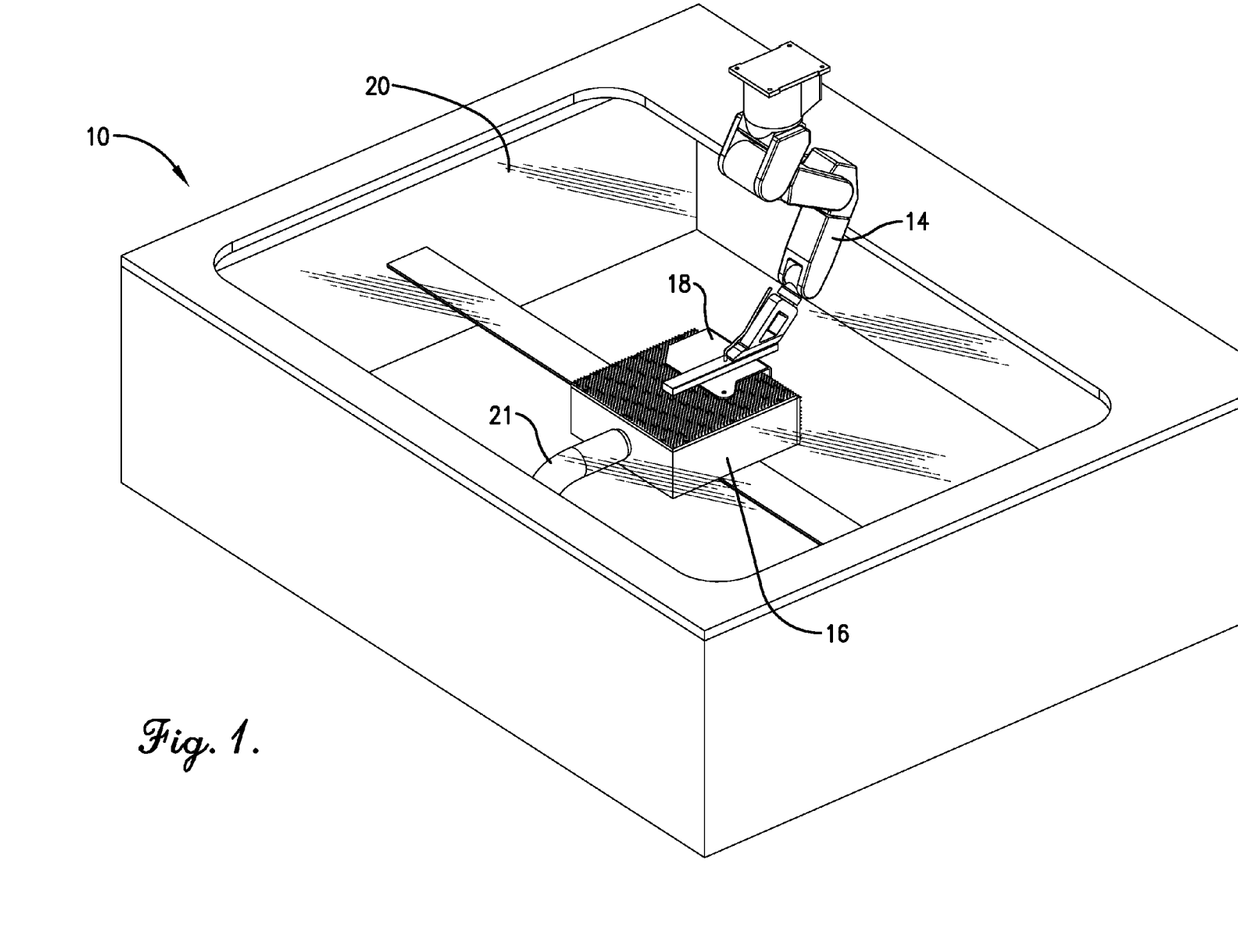
FIG. 1 is a perspective view of an ultrasonic inspection system configured in accordance with embodiments of the invention, the inspection system including a robotic arm for supporting and moving an ultrasonic inspection probe and a part fixture configured to engage and secure a part under inspection without interfering with the inspection process.

Referring now to the drawings, wherein like reference numerals designate identical or corresponding parts throughout the several views, an exemplary nondestructive test system 10 constructed in accordance with embodiments of the invention is illustrated. The system 10 broadly includes an ultrasound probe 12 mounted on a robotic arm 14 and a part fixture 16 positioned proximate the ultrasound probe 12 for securing a part 18 in place during testing. In the illustrated embodiment, the fixture 16 is submerged in a liquid bath 20 and positioned below the ultrasound probe 12. Liquid from the liquid bath 20 fills a gap between the ultrasound probe 12 and the part 18 during inspection of the part 18, providing ultrasonic coupling between the part 18 and the probe 12. Liquid from the liquid bath 20 is also used in securing the part 18 to the fixture 16 during inspection, as explained below in greater detail. In one embodiment the liquid bath 20 is water, but the invention is not so limited and it will be appreciated by those skilled in the art that other liquids may be used. A pump 22 is coupled with the fixture 16 via an egress tube 21 and circulates liquid from the liquid bath 20 through the fixture to secure the part 18 in place against the fixture 16, as explained below.

The robotic arm 14 and probe 12 may be part of a conventional nondestructive inspection system that includes one or more computers for controlling operation of the arm 14 and probe 12. By way of example, the robotic arm 14 may be a standard multi-axis robot manufactured by MOTOMAN ROBOTICS or a similar robotic system. The probe 12 may be manufactured by GEIT and the related computing equipment may be part of a MAUS brand nondestructive inspection system, such as the MAUS V system, using an ultrasonic pulse-echo system. The controlling computer or computers are programmed or configured to actuate the arm 14 such that ultrasonic probe 12 scans all portions of the part 18 to be inspected, including a first wall 24 of the part 18 and a second wall 26 of the part 18. The one or more computers (not shown) control operation of the arm 14 and the probe 12 and generate an image, graph or other indicator of internal characteristics or structure of the part 18 according to the ultrasound test method employed.

Figure 2:
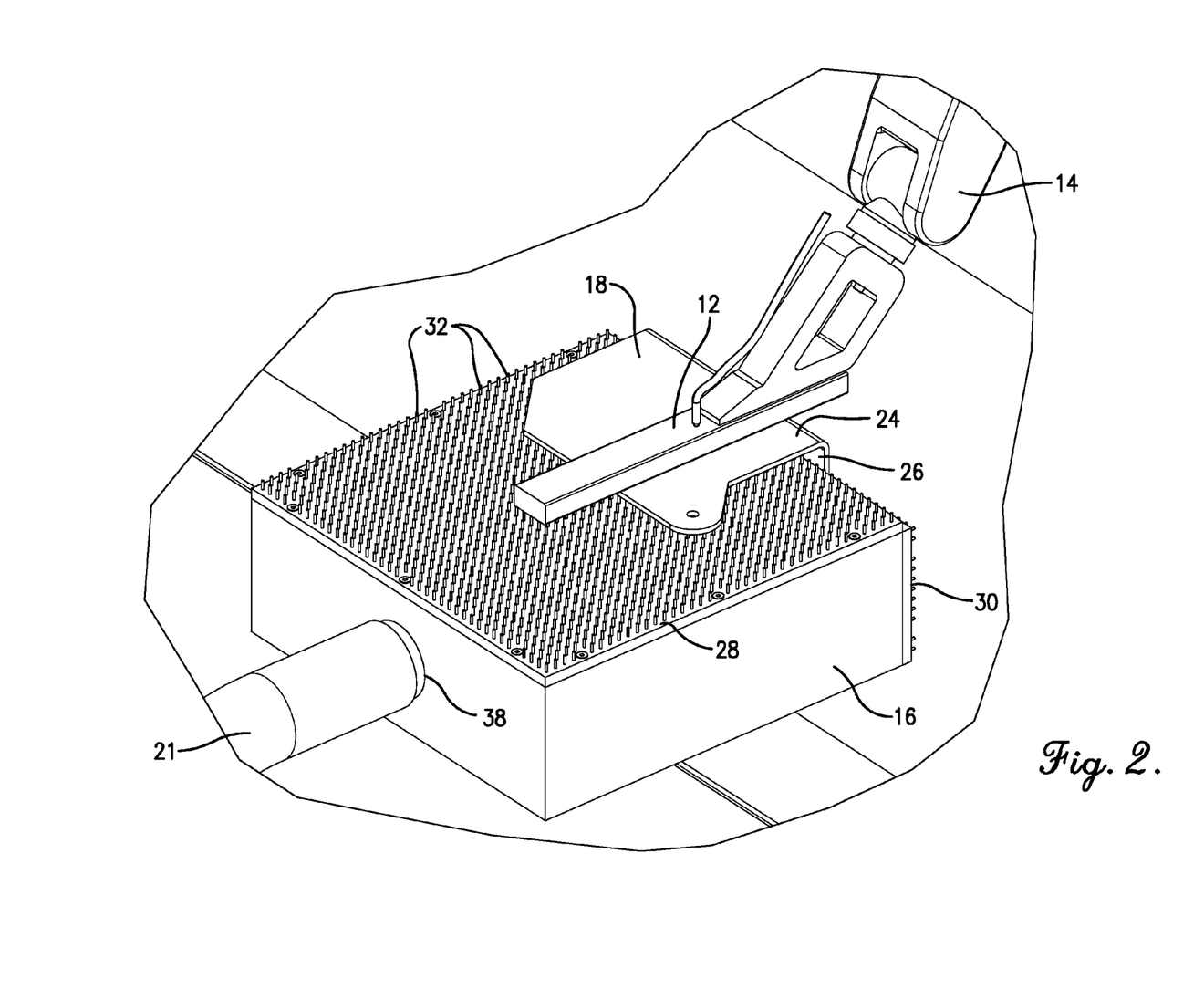
FIG. 2 is an enlarged, fragmentary perspective view of the fixture, part and ultrasonic probe of FIG. 1.
Figure 3:
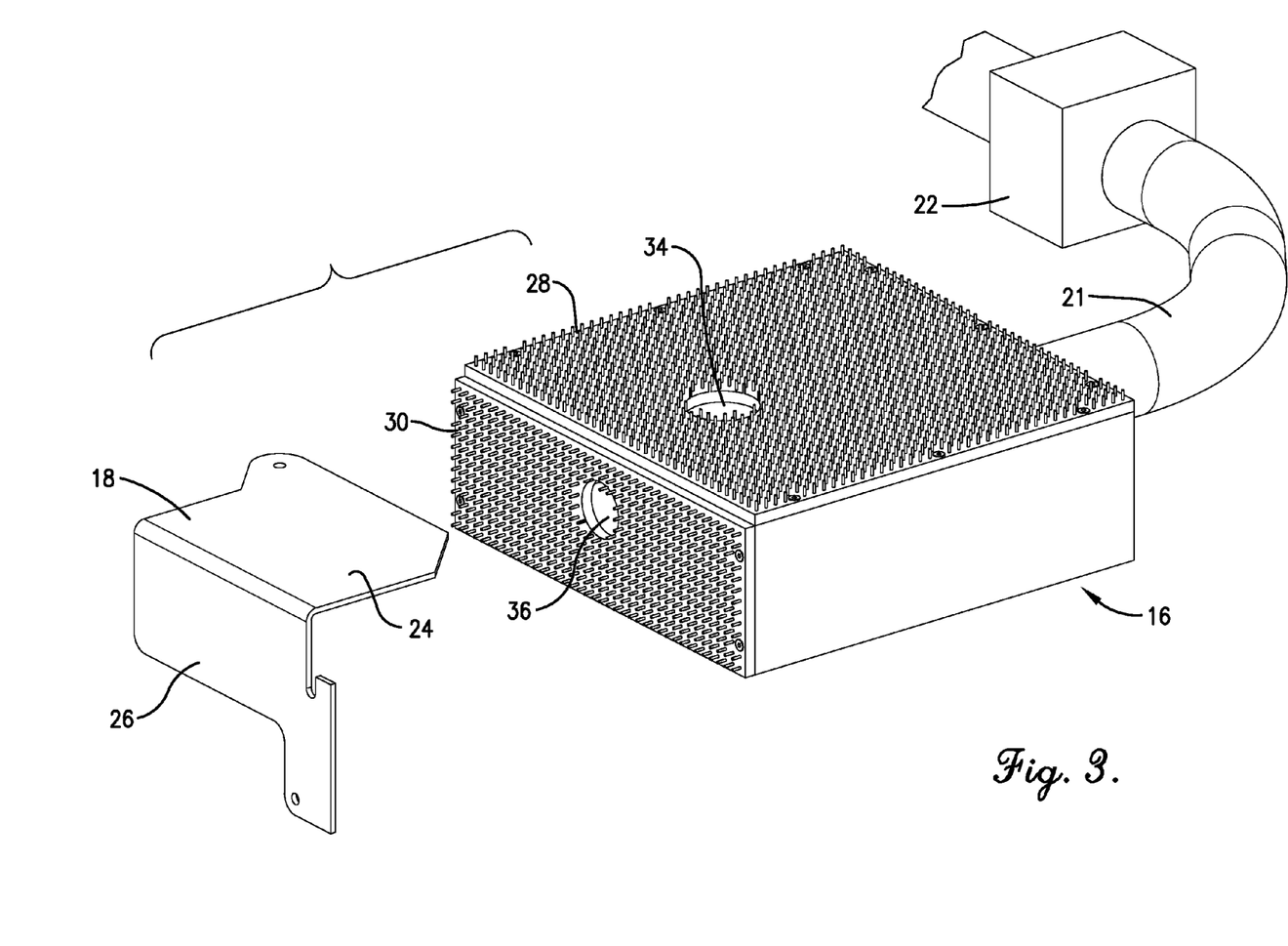
FIG. 3 is a perspective exploded view of the part and the fixture of FIG. 1.

The fixture 16 is configured to engage and secure in place a part under inspection without interfering with the ultrasonic inspection performed by the ultrasound inspection equipment. In other words, the fixture 16—including portions of the fixture 16 in contact with the part 18—is "invisible" to the ultrasound inspection equipment and is not visible or detectable in an image or graph generated by the ultrasonic test equipment. The fixture 16 includes a plurality of work surfaces for securing the part 18 during inspection. In the illustrated embodiment, the fixture 16 includes two planar work surfaces 28, 30 in an orthogonal relationship one to the other. However, the invention is not so limited. One or more of the work surfaces 28, 30 may present a concave or convex curvature, and the surfaces may be positioned at virtually any angle of inclination one relative to the other. As used herein, one surface is at an angle of inclination to another surface if the surfaces are not coplanar and are not parallel. Furthermore, the surfaces may have adjacent edges or may be separated by a space. It will be appreciated that these and other characteristics of the surfaces 28, 30 may vary from one embodiment of the invention to another and depend in part on the shape and configuration of the part being inspected. In the illustrated embodiment, the fixture 16 is configured for operation with the exemplary part 18 that includes the first planar wall 24 and the second planar wall 26 in orthogonal relationship to the first wall 24.

Each of the work surfaces 28, 30 includes a plurality of protrusions 32 for engaging the part, as explained below in greater detail. The protrusions 32 are configured to hold the part 18 at a distance from the surfaces 28, 30 such that there is a space between the part 18 and each of the surfaces 28, 30, thus preventing the surfaces 28, 30 from interfering with the ultrasonic inspection of the part 18. Similarly, the protrusions 32 themselves are configured such that they do not interfere with the ultrasonic inspection of the part 18. Particularly, the protrusions 32 are configured such that portions of the protrusions 32 proximate to or in contact with the part 18 are small enough to avoid detection by the ultrasonic waves emitted by the probe 12.

The fixture 16 further includes an internal channel (not shown) for directing flow of liquid through the fixture 16. The channel includes at least one ingress aperture 34, 36 associated with each work surface 28, 30 and an egress aperture 38 coupled to the pump 22 through the tube 21. The pump 22 induces fluid flow from the liquid bath 20 into the ingress apertures 34, 36, through the internal channel, out the egress aperture 38, and back into the liquid bath 20. Each ingress aperture 34, 36 is positioned and configured such that fluid flow into the ingress aperture results in a fluid pressure differential on a portion of the part 18 positioned proximate the associated work surface 28, 30. Thus, it may be advantageous to place each ingress aperture 34, 36 intermediate at least a portion of the protrusions 32 on the surface 28, 30 wherein the ingress aperture 34, 36 is substantially surrounded by the protrusions 32. While the illustrated ingress apertures 34, 36 each comprise a single, rounded hole positioned approximately in the center of the respective surface 28, 30, it will be appreciated by those skilled in the art that other, equally effective configurations may be used. Multiple smaller apertures may replace each illustrated aperture 34, 36, for example, or a single ingress aperture may be positioned proximate an intersection of the two surfaces 28, 30 to serve both surfaces 28, 30. These and other variations are within the ambit of the present invention.

In the illustrated embodiment, the protrusions 32 are elongated, cylindrical projections approximately equally spaced along each of the work surfaces 28, 30 of the fixture 16. The protrusions 32 are configured to minimize or avoid interference with the ultrasound inspection. Thus, portions of the protrusions 32 proximate the part 18 under inspection, and in particular portions of the protrusions 32 in contact with and engaging the part 18, are of a shape, size or both to avoid detection by the ultrasound inspection equipment. In particular, a portion of each protrusion 32 that is proximate to and in contact with the part 18 is sufficiently narrow to avoid detection by the ultrasound inspection system. To minimize the size of each protrusion 32 at the point of contact with the part and in a region proximate the point of contact, each protrusion 32 may present a tapered end portion 40 terminating in a tip that engages the part 18 under inspection.

Figure 4:
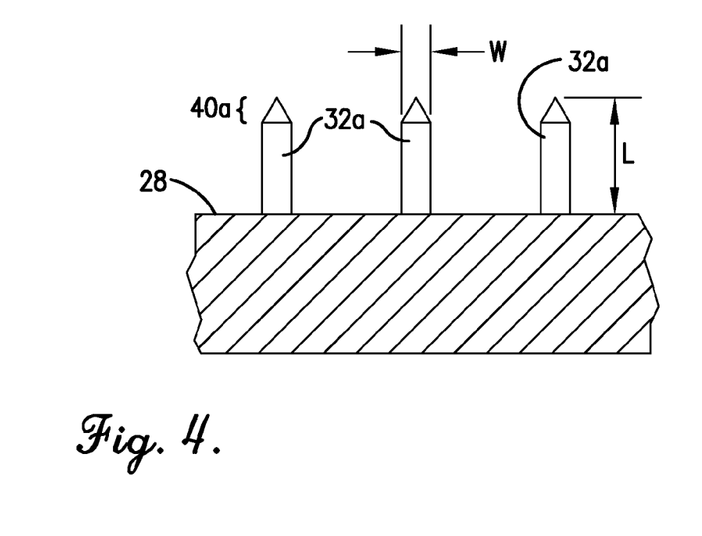
FIG. 4 is an enlarged side elevation, fragmentary, cross-sectional view of the fixture of FIG. 1, illustrating cylindrical protrusions configured according to a first embodiment of the invention and including conical tapered ends terminating in a point.
Figure 5:
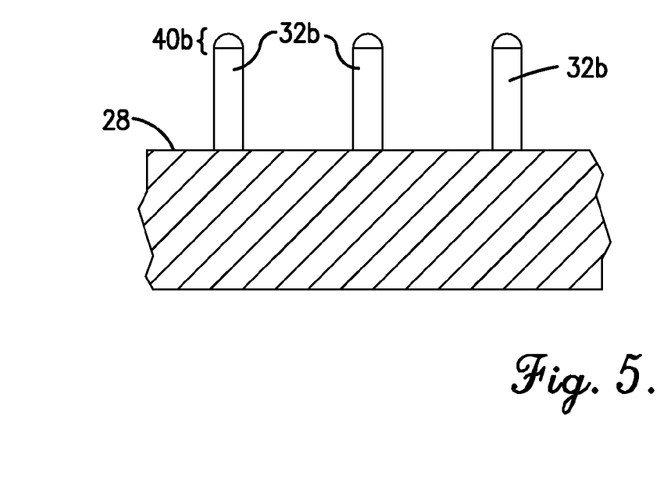
FIG. 5 is an enlarged side elevation, fragmentary, cross-sectional view of the fixture of FIG. 1, illustrating cylindrical protrusions configured according to a second embodiment of the invention and including rounded ends.
Figure 6:
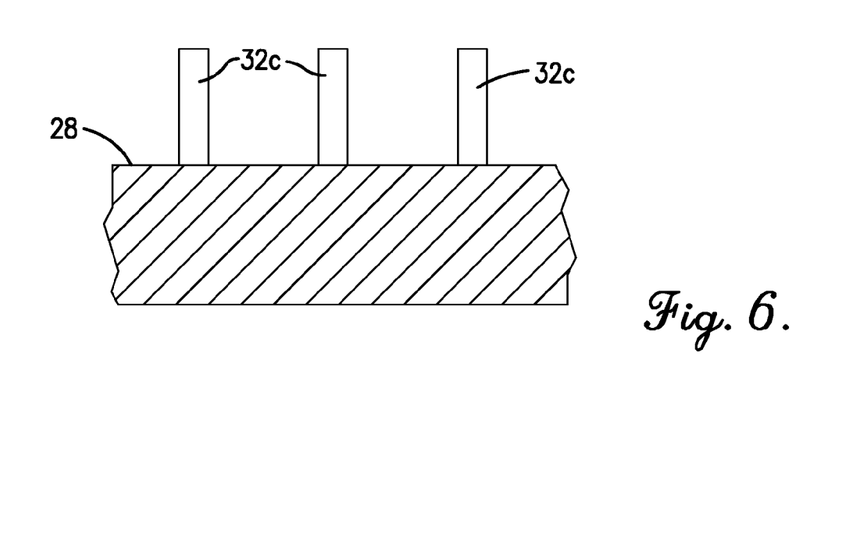
FIG. 6 is an enlarged side elevation, fragmentary, cross-sectional view of the fixture of FIG. 1, illustrating cylindrical protrusions configured according to a third embodiment of the invention, each protrusion including a uniform width from a base to a top.

In a first embodiment illustrated in FIG. 4, each of the protrusions 32a is defined by a cylindrical shank extending from a base that is proximate the surface 28 to a tapered end portion distal the surface 28 and terminating in a pointed tip. In a second embodiment illustrated in FIG. 5, each of the protrusions 32b is similar to the protrusions 32a described above, except that the protrusions 32b of FIG. 5 terminate in a rounded tip rather than a pointed tip. In a third embodiment illustrated in FIG. 6, each of the protrusions 32c is similar to the protrusions 32a and 32b described above, except that the protrusions 32c do not have a tapered end. In other words, each of the protrusions 32c presents a uniform or substantially uniform thickness or cross-section from the base to the tip opposite the base.

The length L of the protrusions 32 should be sufficient to provide adequate separation from the surface to prevent the surface from interfering with the inspection process. The length L of each protrusion 32 should also provide sufficient separation from the surface to allow fluid flow between the part 18 and the surface 28 and into the ingress aperture 34 to secure the part 18 against the surface 28.

In the first illustrated embodiment of the protrusions 32a depicted in FIG. 4, the tapered portion 40a corresponds to a length of the protrusion 32 approximately equal to one-fourth of the total length L of the protrusions 32. In the second illustrated embodiment of the protrusions 32b illustrated in FIG. 5, the tapered portion 40b corresponds to a length of the protrusion 32 approximately equal to one-eighth of the total length L of the protrusions 32. The particular length of the tapered portion of the protrusions is not important to the present invention and may vary from one embodiment to another. By way of example, the tapered portion 40 may correspond to one-tenth, one-eighth, one-fourth, one-third or one-half of a total length of each protrusion 32.

The particular size, shape, spacing and placement pattern of the protrusions 32 may vary substantially from one embodiment of the invention to another without departing from the spirit or scope of the invention. In one exemplary embodiment, the protrusions present a total length L that is preferably within the range of from about 0.001 inches to about 0.5 inches, more preferably within the range of from about 0.01 inches to about 0.3 inches. The total length L may particularly be about 0.1 inches, 0.15 inches, or 0.2 inches. In the exemplary embodiment, the protrusions 32 are separated one from another by a space that is preferably within the range of from about 0.01 inches to about 1.0 inch, more preferably within the range of from about 0.1 inches to about 0.8 inches, and that may particularly be about 0.125 inches, 0.3 inches, 0.4 inches, 0.5 inches, 0.6 inches or 0.75 inches. In the exemplary embodiment, the shank of each protrusion presents a width W that is preferably within the range of from about 0.01 inches to about 0.25 inches and that may particularly be about 0.05 inches or 0.2 inches. The tip of each protrusion presents a thickness that is preferably within the range of from about 0.0001 inches to about 0.1 inches, more preferably within the range of from about 0.001 inches to about 0.01 inches.

In some systems, the detectability of the protrusions 32 by the inspection system depends on the thickness of the protrusions 32 relative to the wavelength of the ultrasonic wave emitted by the probe. By way of example, protrusions presenting a thickness of less than one-quarter of the wavelength of the ultrasound waves generated by the ultrasound probe may be sufficiently narrow to avoid detection by the ultrasonic inspection system. Thus, if the ultrasonic wave emitted by the probe has a wavelength of 0.024 inches, the portion of the protrusion in contact with the part should be less than about one-fourth of that, or less than about 0.006 inches. It will be appreciated that this may vary from one embodiment of the invention to another, and that in other systems the maximum thickness may be one-eighth, one-third or one-half of the wavelength of the ultrasound waves.

The protrusions 32 are preferably constructed of a material or materials that are sufficiently resilient to firmly and securely hold the part 18 against sometimes strong fluid flow without bending or otherwise giving way under the pressure. Thus, the protrusions may be constructed of a metal, such as aluminum or steel, or may be constructed of a suitable plastic such as polypropylene. The protrusions 32 must also be configured to avoid marking, scratching or otherwise damaging or marring the part 18. If the protrusions 32 are constructed of a metal, for example, it may be necessary to use a rounded tip rather than a pointed tip.

Figure 7:
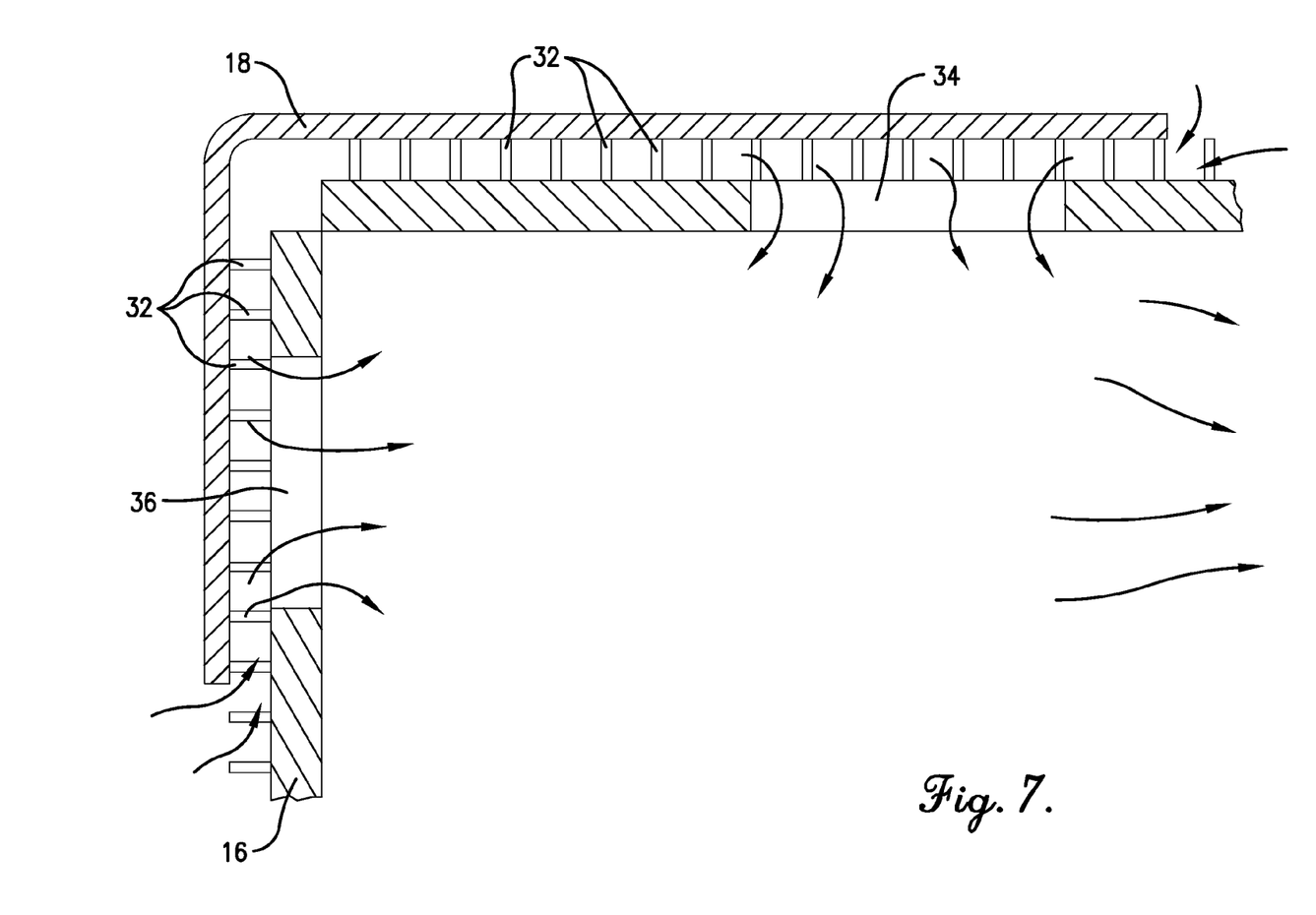
FIG. 7 is a fragmentary cross-sectional view of a portion of the part fixture of FIG. 1, including arrows illustrating the direction of fluid flow around the part and through an ingress aperture of the fixture.

An exemplary fluid flow scheme is illustrated in FIG. 7. Liquid from the liquid bath 20 is pumped through the part fixture 16 such that the liquid flows into the ingress apertures 34, 36 from the liquid bath 20, through the internal channel of the fixture 16, out the egress aperture 38, through the tube 21 and the pump 22, and into the liquid bath 20 where it is recycled through the part fixture 16. The liquid flows around the edges of the part 18 and between the protrusions 32 toward the ingress apertures 34, 36. This fluid flow is caused by a difference in pressure between fluid on the outside of the part 18 and fluid between the part 18 and the fixture 16. This pressure differential, as well as the flow of the fluid, urges the part 18 against the protrusions 32, securing the part in place for the inspection process.

Figure 8:
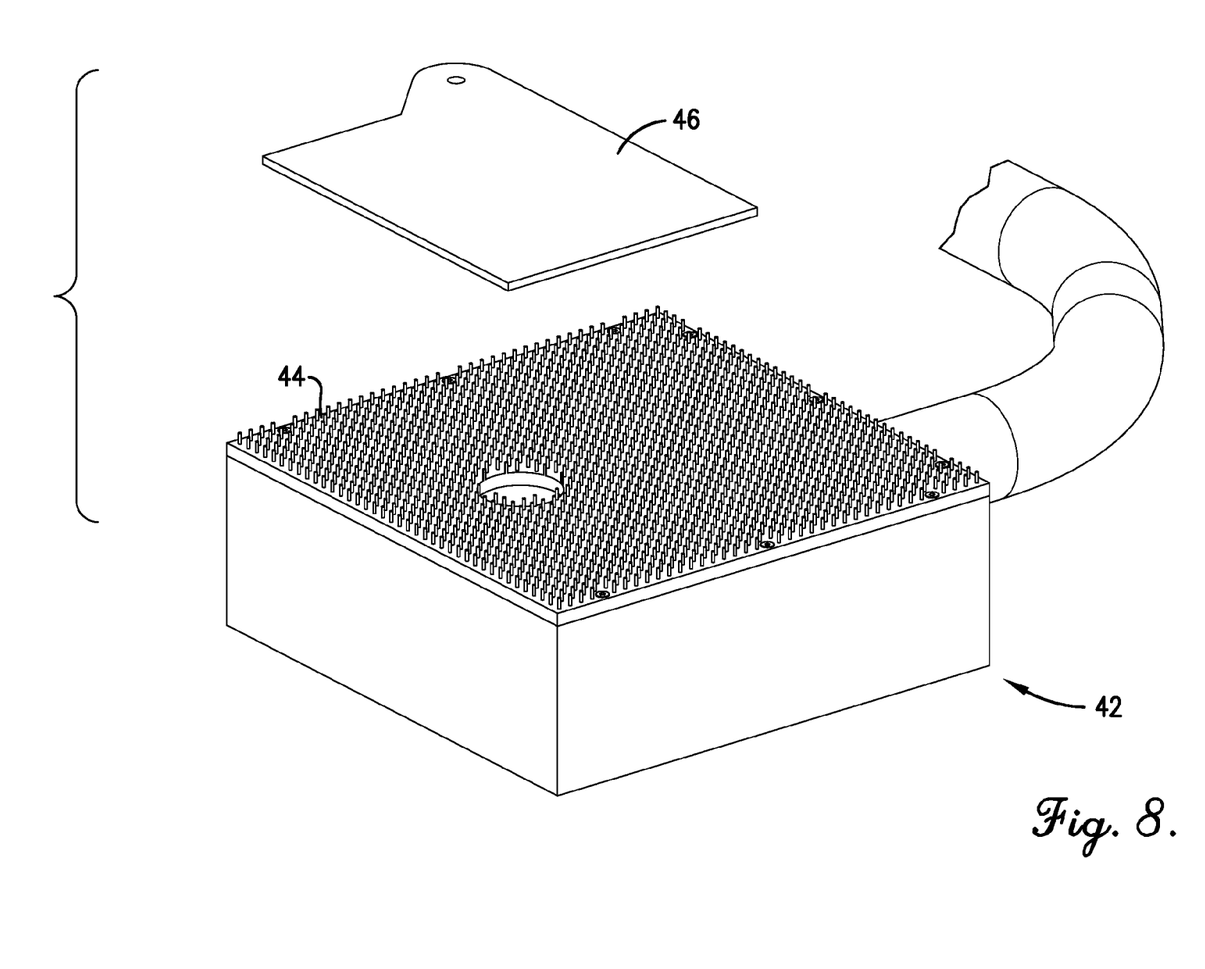
FIG. 8 is a perspective view of a part fixture configured according to a another embodiment of the invention, the part fixture including a single working surface and illustrated with a part including a single wall.

A part fixture 42 constructed according to a second embodiment of the invention is illustrated in FIG. 8. The fixture 42 is similar to the fixture 16 described above, except that the fixture 42 includes a single work surface 44 rather than two surfaces. The surface 44 may be similarly configured to the work surfaces 28, 30 described above, including an ingress aperture and a plurality of protrusions for engaging and securing a part to be inspected. A fixture including a single work surface may be especially well suited for inspection of single-walled or planar parts, such as the part 46 illustrated in FIG. 8.

Figure 9:
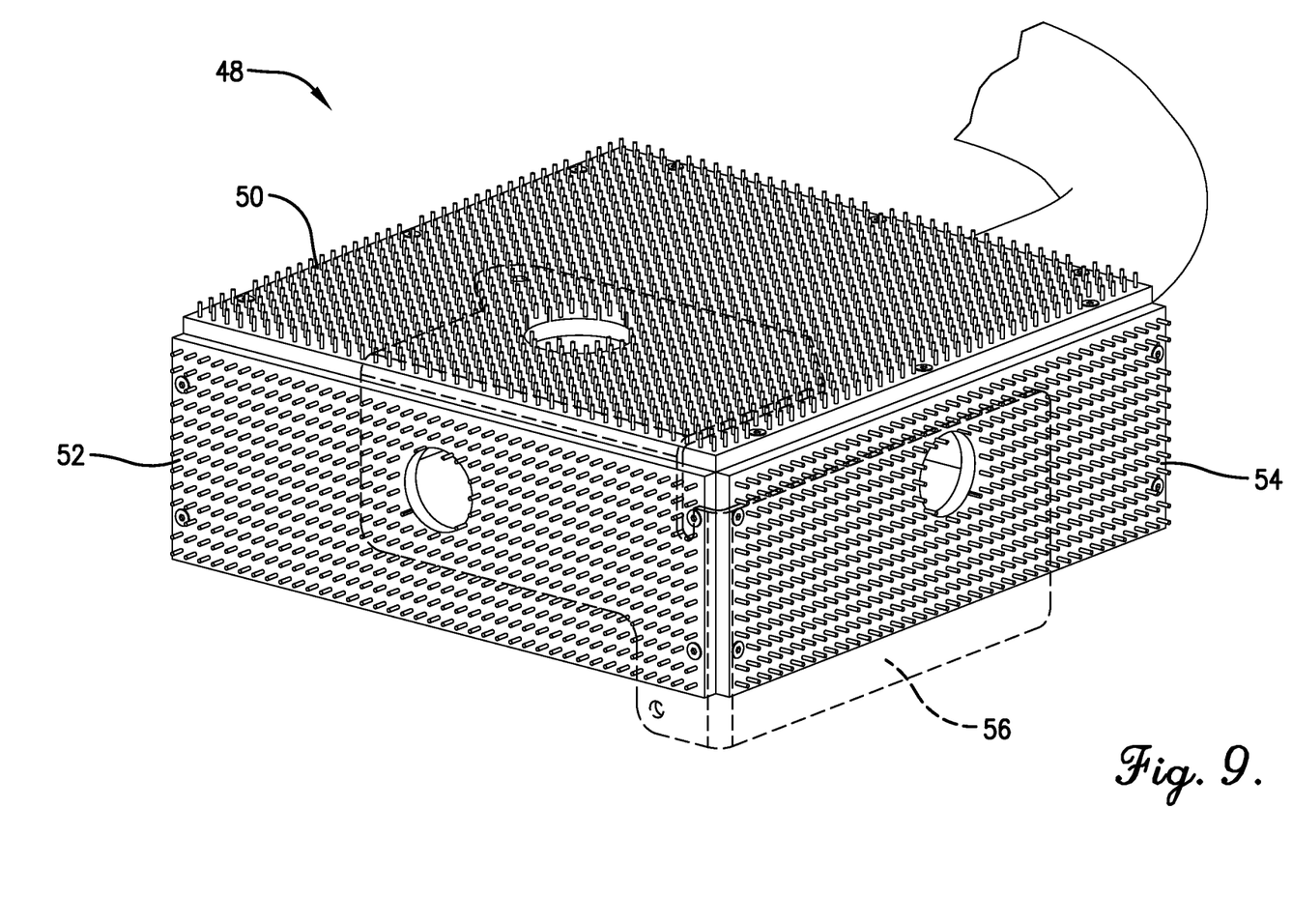
FIG. 9 is a perspective view of a part fixture configured according to a another embodiment of the invention, the part fixture including a three working surfaces and illustrated engaging a part with three walls.

A part fixture 48 constructed according to a third embodiment of the invention is illustrated in FIG. 9. The fixture 48 is similar to the fixture 16 described above, except that the fixture 48 includes three work surfaces 50, 52, 54 rather than two surfaces. Each of the three surfaces 50, 52, 54 may be similarly configured to the work surfaces 28, 30 described above, including an ingress aperture and a plurality of protrusions for engaging and securing a part to be inspected. A fixture including three work surfaces may be well adapted for inspection of three-walled parts, such as the part 56 illustrated in FIG. 8. While the work surfaces 50, 52, 54 of the illustrated fixture 48 are at substantially right angles to one another, it will be appreciated that the invention is not so limited and that each of the surfaces 50, 52, 54 may be positioned at virtually any angle of inclination relative to the other surfaces.

Furthermore, while the fixture 48 is illustrated in use with a three-walled part, it will be appreciated that a fixture with three work surfaces, such as the fixture illustrated in FIG. 9, could be used to inspect single or double-walled parts as well as three-walled parts.

In operation, the pump 22 is activated to circulate liquid from the liquid bath 20 into the ingress apertures 34, 36, through the internal channel of the part fixture 16, out the egress aperture 38 and eventually back into the liquid bath 20 where it may be recycled. With the liquid thus circulating, the part 18 to be inspected is positioned against the protrusions 32 and proximate or over the ingress apertures 34, 36 such that the fluid flow urges the part 18 against the protrusions 32, securing the part 18 in place for inspection. With the part 18 thus secured in place, the inspection system performs the ultrasound inspection by activating the ultrasound probe 12 and moving the probe 12 over the portions of the part 18 to be inspected. When the inspection process is complete the pump 22 is deactivated to stop the flow of the liquid through the fixture 16 and release the part 18. The part 18 is then removed from the liquid bath.

Although the invention has been described with reference to the exemplary embodiments illustrated in the attached drawings, it is noted that equivalents may be employed and substitutions made herein without departing from the scope of the invention as recited in the claims. For example, while the part fixture has been illustrated and described herein with one, two or three work surfaces, the fixture may have virtually any number of work surfaces including four, five or six surfaces. Additionally, while the protrusions are described and illustrated herein as cylindrical, they may take virtually any shape including, for example, shapes with oval or square cross sections.

Having thus described various embodiments of the invention, what is claimed as new and desired to be protected by Letters Patent includes the following:

1. A method of nondestructive inspection of a part, the method comprising:
    submerging a part fixture in a liquid bath, the fixture including a surface, a plurality of protrusions extending from the surface, and a fluid ingress aperture in the surface;
    placing the part on the fixture such that the part is in contact with at least some of the protrusions and is separated from the surface by a space;
    securing the part against the fixture by causing liquid flow into the fluid ingress aperture; and
    performing ultrasonic inspection of the part, by emitting ultrasonic waves from the probe into the part, while the part is secured against the fixture, wherein the ultrasonic waves have a wavelength, wherein portions of the protrusions in contact with the part have a shape or size sufficient to avoid detection by the ultrasonic inspection, wherein a thickness of each of the protrusions at the portion in contact with the part is no greater than one-half of the wavelength of the ultrasonic waves.

2. The method of claim 1, wherein the surface further includes a first surface and a second surface extending at an angle of inclination to the first surface, wherein the protrusions include a first plurality of protrusions extending from the first surface and a second plurality of protrusions extending from the second surface.

3. The method of claim 1, wherein the protrusions each include a tapered or rounded end portion that engages the part during ultrasonic inspection.

\* \* \* \* \*